(12) United States Patent
Tocker et al.

(10) Patent No.: US 10,413,443 B2
(45) Date of Patent: Sep. 17, 2019

(54) THERMAL DEVICE (71) Applicant: Bodychillz Limited, East Sussex (GB)

(72) Inventors: Stephen McCallum Tocker, Sussex (GB); William Howden Simpson, Sussex (GB)

(73) Assignee: BODYCHILLZ LIMITED (GB)

(*) Notice: Subject to any disclaimer, the term of this patent is extended or adjusted under 35 U.S.C. 154(b) by 234 days.

(21) Appl. No.: 15/029,669

(22) PCT Filed: Oct. 16, 2014

(86) PCT No.: PCT/GB2014/053110
§ 371 (c)(1),
(2) Date: Apr. 15, 2016

(87) PCT Pub. No.: WO2015/056019
PCT Pub. Date: Apr. 23, 2015

(65) Prior Publication Data
US 2016/0250066 A1    Sep. 1, 2016

(30) Foreign Application Priority Data

Oct. 18, 2013 (GB) .................................. 1318427.0
Feb. 27, 2014 (GB) .................................. 1403499.5

(51) Int. Cl.
*A61F 7/03* (2006.01)
*A41D 13/005* (2006.01)
*A41D 13/12* (2006.01)
*A62B 17/00* (2006.01)
*A61F 7/10* (2006.01)
(Continued)

(52) U.S. Cl.
CPC ............ *A61F 7/03* (2013.01); *A41D 13/0051* (2013.01); *A41D 13/0053* (2013.01); *A41D 13/1245* (2013.01); *A61F 7/10* (2013.01); *A61F 7/106* (2013.01); *A62B 17/005* (2013.01); *A61F 2007/0018* (2013.01); *A61F 2007/0056* (2013.01); *A61F 2007/0095* (2013.01);
(Continued)

(58) Field of Classification Search
CPC ...................................................... A61F 7/106
See application file for complete search history.

(56) References Cited

U.S. PATENT DOCUMENTS

3,175,558 A * 3/1965 Caillonette ............... A61F 7/03
                                                            126/204
3,871,376 A * 3/1975 Kozak ....................... A61F 7/10
                                                            604/291
(Continued)

*Primary Examiner* — Kaitlyn E Smith
(74) *Attorney, Agent, or Firm* — Jeffrey Joyce, Esq.

(57) ABSTRACT

A thermal device comprising a garment (42A) that may be placed against at least a part of the body (10), the garment (42A) defining at least one enclosed compartment (48, 50) defined between an inner wall (65) and an outer wall (66), and an inlet (21) whereby liquid may be introduced into each such enclosed compartment (48, 50). Each enclosed compartment (48, 50) contains dry material (30) comprising water-soluble chemical compounds that dissolve endothermically or exothermically, and also a compressed sponge (62). There may also be an air bleed valve (64) to bleed any air out of the compartment (48, 50) when water is introduced. The device enables a patient's body to be cooled or heated in emergency, needing only addition of water, and incorporating no toxic or hazardous materials.

15 Claims, 3 Drawing Sheets

(51) Int. Cl.
*A61F 7/00* (2006.01)
*A61F 7/02* (2006.01)

(52) U.S. Cl.
CPC .......... *A61F 2007/0233* (2013.01); *A61F 2007/0234* (2013.01); *A61F 2007/0273* (2013.01)

(56) References Cited

U.S. PATENT DOCUMENTS

| | | | | |
|---|---|---|---|---|
| 3,874,504 A * | 4/1975 | Verakas | ............... | A61F 7/03 126/263.05 |
| 3,882,867 A * | 5/1975 | Moran | ............... | A61D 9/00 604/293 |
| 4,427,010 A * | 1/1984 | Marx | ............... | A61F 7/106 252/70 |
| 4,856,651 A * | 8/1989 | Francis, Jr. | ............... | A61F 7/03 126/263.07 |
| 4,891,501 A * | 1/1990 | Lipton | ............... | A61F 7/02 219/527 |
| 5,178,139 A * | 1/1993 | Angelillo | ............... | A61F 7/03 604/358 |
| 5,277,180 A * | 1/1994 | Angelillo | ............... | A61F 7/03 604/358 |
| 5,300,105 A * | 4/1994 | Owens | ............... | A61F 7/02 607/112 |
| 5,456,704 A * | 10/1995 | Kilcullen | ............... | A61F 7/03 383/901 |
| 5,545,198 A * | 8/1996 | Owens | ............... | A61F 7/02 607/108 |
| 5,575,812 A * | 11/1996 | Owens | ............... | A61F 7/02 607/112 |
| 5,702,375 A * | 12/1997 | Angelillo | ............... | A61F 7/03 602/2 |
| 5,797,892 A * | 8/1998 | Glaug | ............... | A61F 13/42 604/291 |
| 5,817,149 A * | 10/1998 | Owens | ............... | A61F 7/02 607/114 |
| 6,102,937 A * | 8/2000 | Cramer | ............... | A61F 7/03 607/109 |
| 6,123,717 A * | 9/2000 | Davis | ............... | A61F 7/03 607/109 |
| 6,132,454 A | 10/2000 | Fellows | ............... | A61F 7/02 607/108 |
| 6,265,631 B1 * | 7/2001 | Angelillo | ............... | A61F 7/03 602/2 |
| 6,354,099 B1 * | 3/2002 | Bieberich | ............... | A61F 7/0097 607/104 |
| 6,440,160 B1 * | 8/2002 | Cordani | ............... | A61F 7/106 128/870 |
| 6,444,316 B1 * | 9/2002 | Reddy | ............... | B01J 13/22 427/212 |
| 7,338,516 B2 * | 3/2008 | Quincy, III | ............... | C09K 5/18 607/96 |
| 7,707,655 B2 * | 5/2010 | Braunecker | ............... | A61F 7/03 2/206 |
| 7,959,588 B1 * | 6/2011 | Wolpa | ............... | A61F 5/0111 602/13 |
| 9,766,007 B2 * | 9/2017 | Rothenberg | ............... | F25D 5/02 |
| 2003/0097164 A1 * | 5/2003 | Stapf | ............... | A61F 7/034 607/114 |
| 2004/0254549 A1 | 12/2004 | Olson et al. | | |
| 2005/0222651 A1 * | 10/2005 | Jung, Jr. | ............... | A61F 7/02 607/104 |
| 2006/0036304 A1 | 2/2006 | Cordani et al. | | |
| 2006/0142828 A1 * | 6/2006 | Schorr | ............... | A61F 7/034 607/108 |
| 2006/0161231 A1 * | 7/2006 | Cazzini | ............... | A61F 7/0097 607/104 |
| 2007/0106356 A1 * | 5/2007 | Carstens | ............... | A41D 13/005 607/112 |
| 2007/0142883 A1 * | 6/2007 | Quincy, III | ............... | A61F 7/03 607/96 |
| 2007/0150033 A1 * | 6/2007 | Johnson | ............... | A61F 7/106 607/114 |
| 2008/0147152 A1 * | 6/2008 | Quincy | ............... | A61F 7/03 607/112 |
| 2008/0147153 A1 | 6/2008 | Quincy et al. | | |
| 2008/0200971 A1 * | 8/2008 | Dodo | ............... | A61F 7/034 607/108 |
| 2009/0062890 A1 * | 3/2009 | Ugajin | ............... | A61F 7/034 607/104 |
| 2009/0287280 A1 * | 11/2009 | Wong | ............... | A61F 7/034 607/96 |
| 2009/0287283 A1 * | 11/2009 | Biser | ............... | A61F 7/02 607/109 |
| 2010/0087902 A1 * | 4/2010 | Ota | ............... | A61F 7/034 607/112 |
| 2011/0046527 A1 * | 2/2011 | Sandhu | ............... | A61F 5/055 602/14 |
| 2011/0307041 A1 * | 12/2011 | Floyd | ............... | A61F 7/10 607/109 |
| 2012/0053546 A1 * | 3/2012 | Fogg | ............... | A61F 7/10 604/367 |
| 2012/0157904 A1 * | 6/2012 | Stein | ............... | A61F 7/02 602/43 |
| 2012/0232622 A1 * | 9/2012 | Kriksunov | ............... | A61F 7/034 607/114 |
| 2013/0172790 A1 * | 7/2013 | Badawi | ............... | A61F 7/02 601/15 |
| 2014/0039584 A1 * | 2/2014 | Potter | ............... | A61F 7/0097 607/114 |
| 2016/0095743 A1 * | 4/2016 | Jackson | ............... | A61F 7/02 607/108 |
| 2016/0166424 A1 * | 6/2016 | Hanuka | ............... | A61F 5/4407 604/333 |
| 2018/0221511 A1 * | 8/2018 | Ohri | ............... | A61K 31/445 |

\* cited by examiner

THERMAL DEVICE

The invention relates to a thermal device, which may be a cooling device that may for example be used to cool a patient's body in the event of medical need, for example where a patient has suffered a cardiac arrest, or is suffering from heat exhaustion, or a heating device which may be used to heat a patient's body, for example if a patient is suffering from hypothermia.

There are a variety of medical conditions in which it has been found that cooling a patient's body is beneficial. For example such treatment may be beneficial in the emergency treatment of patients who have suffered from a cardiac arrest. After treatment leading to return of spontaneous circulation, lowering the patient's body temperature to achieve managed hypothermia will reduce the patient's metabolic rate, and suppress at least some of the adverse effects. Consequently it would be advantageous to provide a body cooling device which could be carried in an ambulance and used to treat the patient in the immediate aftermath of the cardiac arrest. A cooling device that does not require a source of power to provide the cooling effect would be advantageous in that it does not require connection to any source of power, so for example it could be used with a patient being carried on a stretcher, and it would be readily portable.

Although primarily envisaged as being intended for thermal treatment of a human body, it will be appreciated that such a device may also be applicable in a veterinary context, for example to cool the body of a warm-blooded animal.

According to the present invention there is provided a thermal device comprising a garment that may be placed against at least a part of a body, the garment defining at least one enclosed compartment defined between an inner wall and an outer wall, and means whereby liquid may be introduced into each such enclosed compartment, wherein each enclosed compartment contains dry material comprising at least one soluble chemical compound that dissolves endothermically or exothermically in the liquid, and also at least one element of a compressed sponge.

Where the thermal device is a cooling device, the dry material must dissolve endothermically, whereas where it is a heating device the dry material must dissolve exothermically. The liquid may advantageously be water, as this is readily available. By way of example, for a heating device the dry material may comprise calcium chloride, calcium acetate or lithium bromide, which are salts that dissolve exothermically; another option would be sodium hydroxide, although this is less preferred because of its caustic properties (in the event of a leak). The quantity of liquid added, and the quantity of dry material, may be such as to approach a saturated solution.

In one embodiment the dry material comprises at least two compounds that dissolve endothermically. It is preferred if the compounds comprise a covalently-bonded molecular compound and an ionic compound. Where the liquid is water, urea is suitable as a covalently-bonded compound; and there are a range of different ionic compounds, such as ammonium chloride, ammonium nitrate, ammonium nitrite, ammonium cyanate, ammonium thiocyanate, potassium nitrate, potassium nitrate, potassium cyanate, potassium thiocyanate, sodium chlorate, sodium nitrate, sodium nitrite, sodium cyanate or sodium thiocyanate. All of these compounds dissolve endothermically in water, and would lead to a significant degree of cooling. From a practical perspective it is desirable to avoid any compounds that may be toxic or potentially unstable, or that are components of explosive mixtures. The preferred compounds are urea and ammonium chloride, and the amounts of each compound may be at least 90% of the amount required for a saturated solution at an operating temperature (such as say 10° C., in the case of a cooling device).

The inner wall and the outer wall may be flexible, and may be waterproof, so liquid that has been introduced into the enclosed compartment cannot subsequently leak out through the walls during use of the device. The enclosed compartments may be at least partially evacuated, after introduction of the soluble compound, to prevent air pockets on filling with liquid.

In addition, each enclosed compartment also contains at least one element of a compressed sponge. For example each enclosed compartment may contain a layer or sheet of compressed sponge. The sheet may be included as part of a pre-cut template such that it can be welded between the two layers during production. Such a compressed sponge may initially, when dry, extend throughout the area of the enclosed compartment; when a liquid such as water is introduced into the enclosed compartment, it is absorbed by the sponge, which rapidly expands in thickness, so the volume of the sponge increases, and it may for example expand to occupy the entire volume of the enclosed compartment. Alternatively each enclosed compartment may contain multiple compressed sponge elements, such as pellets or discs.

Preferably the thermal device is in the form of a garment that may be placed around at least part of the body, for example around a torso. The means to introduce the liquid may be an inlet. The thermal device may also include a liquid reservoir for connection to the inlet. Such a reservoir may be detachable from the garment. The means for attaching and detaching the reservoir from the garment may be a non-spill quick-disconnect coupling so the coupling can be attached and detached without leakage.

At least one enclosed compartment may also include a valve to enable any air within the enclosed compartment to be released when a liquid such as water is introduced into that compartment. Such an air bleed valve may be actuated manually, or alternatively may be automated to allow air to bleed out, but to close when a liquid such as water enters the valve. For example such an automated valve may be entirely mechanical, and include one or more hygroscopic discs which allow air to flow when dry, but which expand to obstruct the flow when in contact with water; such an automated valve is similar to automatic radiator bleeding valves, which may be referred to as auto-venting valves. Alternatively the garment may include areas of hydrophobic film through which air can pass but not liquid, as such a material would fulfil the same purpose as an auto-venting valve. It will be appreciated that the presence of compressed foam implies the presence of some air in the compartment, initially, but that the quantity of air is considerably less than would be present in expanded foam.

If the liquid is introduced separately into each enclosed compartment, then each enclosed compartment may be provided with such an air bleed valve or an area of air-permeable hydrophobic film; but if the liquid is introduced through a common inlet into a number of enclosed compartments that are interconnected, for example in series, a single air bleed valve or area of air-permeable hydrophobic film may be arranged so that air is allowed to leave all of those enclosed compartments through the air bleed valve or film, as a liquid such as water is introduced into those enclosed compartments, and may for example be provided in a compartment that is remote from the enclosed compartment into which the liquid is initially introduced. Such a layout would have the effect of maximising the volume of air exhausted.

Urea and ammonium chloride are soluble in water, and in each case the dissolution is an endothermic process. The liquid to be added into each enclosed compartment may therefore be water. Urea dissolves in the form of molecules, each molecule becoming hydrated; whereas ammonium chloride dissolves in the form of ions, each ion becoming hydrated. Because one compound dissolves in molecular form whereas the other dissolves in ionic form, the dissolution of one compound does not significantly interfere with the dissolution of the other.

It will be appreciated that both urea and ammonium chloride are of low toxicity, and are non-flammable. They do not provide a security risk, as they are not associated with explosives. In contrast, although the dissolution of materials such as potassium nitrate or ammonium nitrate would also be endothermic, these materials may be perceived as introducing a security risk because of their association with explosives: potassium nitrate is a component of gunpowder, while ammonium nitrate when mixed with a fuel such as oil or sugar is also explosive. So the compounds within each enclosed compartment may be selected to not include ammonium nitrate or nitrates that form oxygen gas on thermal decomposition or detonation by shock: the proportion of such oxygen-generating nitrates within the dry material should be no more than 3%, preferably no more than 1%, and more preferably no more than 0.5%.

Although this is not essential, it is desirable if both the urea and the ammonium chloride are chemically pure, i.e. with less than 5% impurities, preferably less than 2% impurities, and more preferably less than 0.5% impurities; and it is also desirable if the water that is introduced is also pure. The purity of the urea may be indicated by its melting point, as the melting point of pure urea is 133-135° C., while that of commercially-available urea is typically between 116 and 125° C., and the urea used in the dry material preferably has a melting point of above 126° C. The dry material may also include a gelling agent, such as polyacrylic acid or hydroxypropyl methyl cellulose, although other gelling agents such as acacia gum, alginic acid, carrageenan, locust bean gum, pectin or gelatin may also be used.

The chemical compounds present in the dry material may be of substantially uniform particle sizes, or may be provided with a range of different particle sizes. At least some of the particles may be encapsulated in a water-soluble or water-permeable coating to slow down the dissolution process, so it takes place over a longer period. This may apply to the chemical compounds or to the gelling agent or to a combination of them.

The garment may for example be in the form of a waistcoat or jacket. It may define a single enclosed compartment, if the entire garment is double walled. Alternatively it may define a plurality of enclosed compartments. For example if it is in the form of a waistcoat, it may define a rear enclosed compartment, and two front enclosed compartments, on the left and right respectively. As another example a waistcoat may define separate enclosed compartments for example one around the neck, one around the lower back, and at the front one on either side adjacent to the stomach. In another example a waistcoat may define separate enclosed compartments, one around the neck, one under each armpit, and one on either side of the stomach. Where there are a number of compartments, they may be interlinked by liquid flow channels. The various compartments may be structurally linked by sheet material; or may be structurally connected by narrow bands of material, so forming a skeletal structure.

The garment may include a hood, and may include one or more enclosed compartments in the hood that will therefore be adjacent to the patient's head when wearing the garment.

The garment may also include a layer of thermal insulation, for example a layer of thermal insulation outside the outer wall of each enclosed compartment, so that the dissolution process within the enclosed compartment primarily extracts heat from, or provides heat to, the patient rather than from the surroundings. The insulation layer may be a separate layer additional to the outer wall, or may be integral with the outer wall, for example by using polymer coated textile or flock as the outer wall, with the polymer coating on the inside to form an impermeable layer. The garment may include a layer of thermal insulation between the inner face of the garment and the inner wall of each enclosed compartment, to ensure the thermal effect is not excessive when the device is at its coldest or hottest temperature, while ensuring that the therapeutic period is maximised without risk to the patient.

In order to bring about the thermal effect, a liquid solvent such as water must be introduced into the enclosed compartments. If the garment does not initially contain any water, it is comparatively lightweight. Activation of the thermal effect only requires water, which is readily available. Tap water has been found to be satisfactory for this purpose, although deionised water is slightly more effective. Water that contains significant quantities of dissolved material, such as sea water, would be less effective. In an alternative the water may be provided within the garment, for example in a separate container or a sachet, which may be either inside or outside the enclosed compartment, although this increases the initial weight of the garment.

Each enclosed compartment may be such that when completely filled with the liquid solvent, each compartment contains a ratio of chemical compound to liquid that provides the most effective thermal effect, and provides a saturated solution.

In one embodiment the garment includes a single inlet through which the liquid can be introduced into a plurality of enclosed compartments; such a single inlet may enable liquid to be introduced into all the enclosed compartments. The inlet, or each inlet, may incorporate a non-return valve so that liquid or solution cannot flow out of the enclosed compartments once it has been introduced. Each inlet may also be initially covered by a gas-tight seal, which must be removed or perforated in order to introduce the liquid, so preventing the ingress of air during storage.

In another aspect the present invention provides a method of cooling or heating a body by use of such a thermal device, which may be in the form of a garment.

Although primarily envisaged in the context of treating a living creature or a person, it will be appreciated that the invention may also be applicable in subjecting inanimate objects to a thermal effect. So in a further aspect the present invention provides a thermal device defining at least one enclosed compartment defined between an inner wall and an outer wall, and means whereby liquid may be introduced into each such enclosed compartment, wherein each enclosed compartment contains dry material comprising at least one soluble chemical compound that dissolves endothermically or exothermically in the liquid, and also at least one element of a compressed sponge. As discussed above, in the case of a cooling device the chemical compounds may comprise a covalently-bonded molecular compound and an ionic compound, so that suitable compounds are urea and ammonium chloride in this context also. The subsidiary aspects of the garment discussed above are also applicable in this aspect of the invention, mutatis mutandis. Depending on the application, the inner wall and the outer wall may be rigid or flexible. For example such a cooling device may be used to cool a bottle containing a drink.

Furthermore the invention is also applicable in the form of an "instant ice pack", the pack comprising an enclosed compartment containing the dry material that dissolves endothermically, and the compressed sponge, as described above, where the pack also comprises a container or sachet of water which is arranged so the water can be brought into contact with the dry material in the enclosed compartment for example by breaking the sachet. Although providing the requisite water in the pack increases its weight, it ensures that the pack can be activated whenever required, without first having to obtain water. On the other hand, in the context of a cooling garment that may be utilised in an ambulance or a hospital, for example, it may be preferable not to incorporate the water in the garment initially, so as to reduce the initial weight, as in this case arrangements can be made to ensure that water is available in the ambulance or hospital for this and for other purposes.

The invention will now be further and more particularly described, by way of example only, and with reference to the accompanying drawings in which.

The invention will primarily be described in relation to a cooling garment, but it will be appreciated that by changing the nature of the dry materials that undergo dissolution, substantially the same garment may be used as a heating garment.

Figure 1:
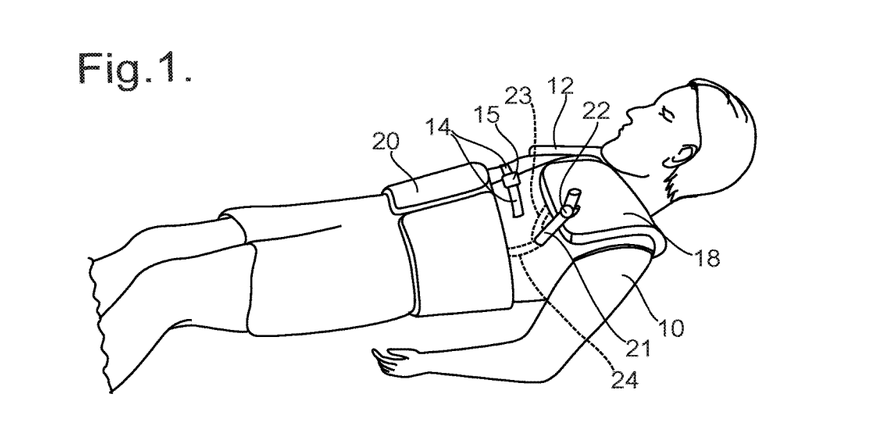
FIG. 1 shows a perspective view of a patient wearing a cooling garment of the invention.

Referring to FIG. 1 a patient 10 is shown wearing a garment 12 in the form of a sleeveless jacket coming down to the patient's waist. The garment 12 opens at the front, so that it is easy to fit the garment 12 onto the patient 10, and the left and right sides of the front of the garment 12 are fastened together by straps 14 with a quick-release fastener 15. The garment 12 is shown as incorporating a single pair of straps 14 and a fastener 15, although there may be more than one such fastener 15. The parts of the garment 12 around the neck and shoulders of the patient 10 define an enclosed compartment or enclosure 18, while the parts of the garment 12 around the stomach of the patient 10 define an enclosure 20. The garment 12 also includes an inlet tube 21 with an inlet valve 22 through which water can be introduced into the enclosures 18 and 20 through respective channels 23 and 24 (shown schematically). The garment 12 may also be provided with straps (not shown), one on each side, so it can be secured to a stretcher.

Figure 2:
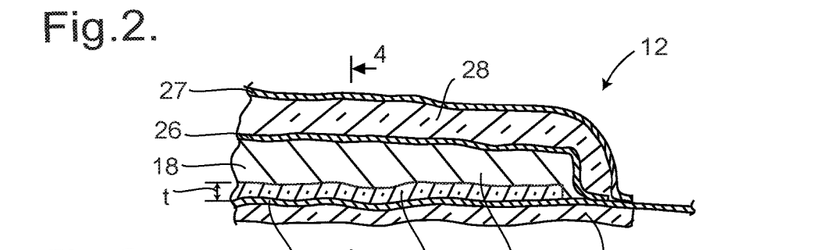
FIG. 2 shows a schematic cross-sectional view through a part of the garment of FIG. 1.

Referring now to FIG. 2, this shows a sectional view through a part of the enclosure 18; the enclosure 20 has an identical structure. The garment 12 includes an inner flexible sheet 25 of a polymer, an outer flexible sheet 26 of a polymer, so that the enclosure 18 is defined between the inner flexible sheet 25 and the outer flexible sheet 26; and a second outer flexible sheet 27 of a polymer separated from the outer flexible sheet 26 by a flexible layer 28 of thermal insulation. Around the edges of the enclosure 18 the second outer flexible sheet 27 and the outer flexible sheet 26 are welded to the inner flexible sheet 25. A layer 29 of thermal insulation, for example felt, is bonded to the inner flexible sheet 25, between the inner flexible sheet 25 of the enclosure 18 and the inner face of the garment 12.

The enclosure 18 contains a sheet 60 of compressed sponge, for example a compressed cellulose sponge, and also contains a dry material 30 which consists of urea and ammonium chloride, in powder form or granular form, and mixed together. The sheet 60 occupies substantially the entire area of each enclosure 18 and 20, but only a small proportion of its thickness; the initial thickness, t, may for example be less than 10 mm, for example 2 mm or 4 mm. When water is introduced into the enclosures 18 and 20, the sheet 60 expands in thickness, and may for example then occupy substantially the entire volume of the enclosure 18 or 20, the expanded sponge having an open cellular structure, and the cells of the sponge containing the aqueous solution of the materials that had constituted the dry material 30. The dry material 30 may optionally also include a gelling agent such as polyacrylic acid, and this may be encapsulated in a water-soluble barrier material such as gelatin.

The dry material 30 substantially fills the enclosure 18, apart from the volume occupied by the sheet 60, although it will be appreciated that because the inner and outer sheets 25 and 26 are flexible, the volume of the enclosure 18 can increase when water is subsequently introduced.

The polymer of the flexible sheets 25, 26 and 27 may for example be polyethylene, either high-density or low-density, although other polymers may also be used, for example polypropylene, polyester or polyurethane. At least some of the flexible sheets 25, 26 and 27 may have metallised surfaces. The metallised surfaces on the flexible sheets 26 and 27 suppress heat transfer to or from the surroundings, as does the layer 28 of thermal insulation.

When in use on a patient 10, water is introduced through the inlet tube 21 into the enclosures 18 and 20, where the dry material 30 dissolves endothermically in the water, reducing the body temperature of the patient 10. The flexible layer 28 suppresses heat flow from the surroundings, whereas the insulation layer 29 makes the heat transfer from the patient 10 more uniform over the area of the enclosure 18 or 20.

If the garment 12 is modified to omit the insulation layer 29, it will be appreciated that the material that comes into contact with the patient 10 would be the inner surface of the flexible sheet 25. Clearly the inner flexible sheet 25 and the outer flexible sheet 26 must be impermeable to liquid water, so there is no potential for accidental leakage. Furthermore the garment 12 should be comfortable to the patient 10, and not cause irritation or abrasion, as it may be placed on a grazed or wounded region of the patient's skin. In some embodiments the garment 12 may include a layer of fabric (not shown), either woven or nonwoven, which would be in contact with the patient 10 during use, to which the flexible sheet 25 is bonded to provide impermeability in the regions that define the enclosures 18 and 20.

It will also be understood that the quantity of dry material 30 must be sufficient to achieve the desired degree of cooling, which from a medical perspective preferably reduces the core body temperature to less than 36° C., for example to between 32 and 34° C. However, the garment 12 is envisaged as being for cooling a patient who is being taken to a hospital; and further cooling may then be provided in hospital to reach such temperatures. Consequently it may be sufficient if the garment 12 can at least start the cooling process, and maintain cooling for at least one hour. By way of example, in the course of one hour the core body temperature in some patients may be decreased by 0.5° C., but the exact figure will naturally vary between different patients. Furthermore the distribution of the endothermic effect should be as even as possible, rather than being localised. This uniformity of cooling may be enhanced by subdividing the enclosures 18 and 20 into compartments, and supplying water separately to each subdivision or compartment, or ensuring the water is distributed evenly to the compartments.

The provision of the sheet 60 has been found to provide several advantages. It improves the texture of the garment 12, so that it is closer to that of a blanket. It improves the impact resistance of the enclosures 18 and 20, as the resulting sponge can deform when impacted; and it reduces the extent of leakage in the event of an enclosure 18 or 20 being punctured. It suppresses the tendency of water or aqueous solution flowing around within an enclosure 18 or 20, and indeed it has been found to reduce the extent to which the dry material 30 moves around in an enclosure 18 or 20 before any water is introduced. It also tends to absorb any water that is present, and so enhances the distribution of water throughout the enclosure or enclosures 18 and 20 of the garment 12.

It will be appreciated that instead of providing compressed sponge in the form of a single sheet 60, each compartment 18 and 20 may instead include several separate compressed sponge elements such as pellets or discs. Such elements may be mixed in with the dry material 30. This alternative arrangement provides at least some of the benefits of the single sheet 60.

The garment 12 may also be modified by providing a larger number of separate enclosures, equivalent to the enclosures 18 and 20, adjacent to particular parts of the anatomy where cooling is particularly required. In one example there might be an enclosure at the back of the patient's neck; enclosures on each side of the patient's neck; and enclosures under each armpit. There might also be such enclosures around the groin and the head of the patient 10.

The garment 12 shown in FIG. 1 includes the enclosures 18 and 20, and linking portions which may consist solely of the flexible sheet 25, or which may also include a layer of fabric (not shown) as mentioned above. In a modification the enclosures such as 18 and 20 are connected together by discrete straps rather than by a sheet, so forming a skeletal structure linking together all the enclosures (such as the enclosures 18 and 20), and the inlet tube 21.

The following paragraphs review the chemical compounds that might be suitable for use in the cooling device. When comparing different chemical compounds that might be incorporated in the dry mixture 30, in addition to considering toxicity, significant considerations are the enthalpy change on dissolution, Q (measured in kJ/mole); the molar mass M; and the solubility, S (in g/100 mL of solution). The heat H absorbed during dissolution to saturation (forming 100 mL of solution) is clearly given by:

$$H = Q \times (S/N)$$

The resultant change of temperature of the water can be estimated by assuming that the solution has a specific heat capacity the same as that of water. Some examples of the heat absorption, H, and the resulting temperature change, $\Delta T$, calculated in this way are shown in the following table:

TABLE 1

| Compound | H/kJ | $\Delta T/K$ |
|---|---|---|
| urea | 26.97 | −31 |
| potassium nitrate | 10.91 | −20 |
| sodium chloride | 2.38 | −4 |
| ammonium chloride | 8.21 | −15 |
| ammonium nitrate | 48.13 | −46 |

From these figures it will be appreciated that ammonium nitrate and potassium nitrate would produce a large temperature reduction. However, as previously commented, both these compounds would produce oxygen gas when subjected to thermal decomposition or shock detonation, and are associated with explosive mixtures. For this reason they are excluded as being unsuitable. Sodium chloride on the other hand is excluded as producing a smaller temperature reduction than the other compounds. Various other chemical compounds (not listed) have been excluded because they are toxic, unstable, insufficiently endothermic, or incompatible with other materials.

It will be appreciated that where two chemical compounds are to be dissolved, if both the compounds are salts and therefore ionic, the cooling produced by a second salt is substantially reduced if the solution is already saturated with a first salt. In contrast, if the compounds are of different types, one being a salt and the other being molecular, i.e. covalently bonded, when a solution is saturated with one compound the other can still be effectively dissolved in the solution to substantially the same degree as being dissolved in water. For example urea (a molecular substance) can be added to a solution already saturated with ammonium nitrate (ionic) or vice versa, after the solution has returned to ambient temperature. The cooling provided and the degree of dissolution with the second compound are almost indistinguishable from those that occur when the second compound is added to pure water. It will be apparent that this effect may allow cooling to a greater degree than would be achievable with a single ionic or molecular compound. This effect might also be used to extend the duration of cooling instead of the depth for example by filling different compartments with different chemicals and allowing the liquid to diffuse between them thereby mixing and dissolving the two compounds more gradually.

Figure 3:
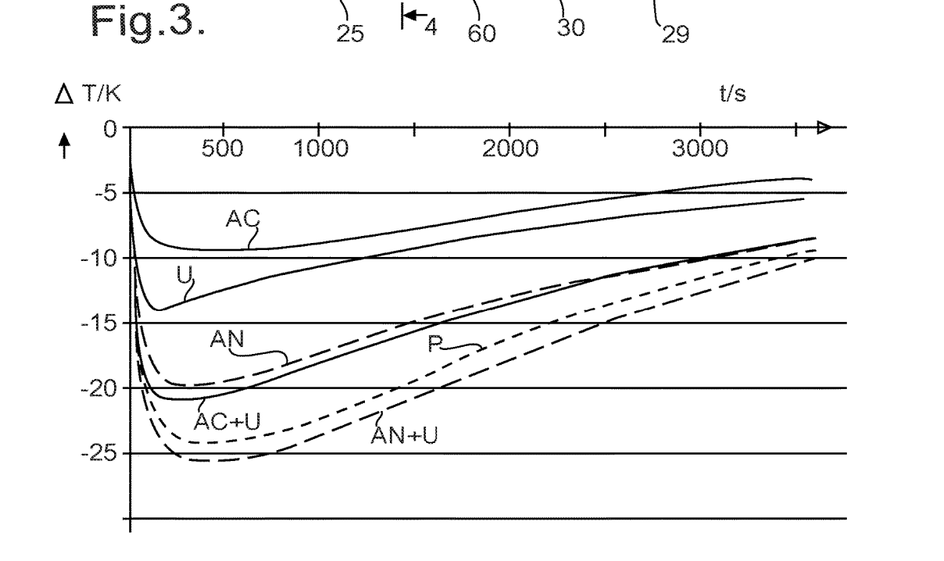
FIG. 3 shows graphically the temperature change brought about on dissolution of various chemical compounds.

Consequently there is a benefit in providing two chemical compounds, one of which is molecular in form and the other is ionic. This is illustrated in the graphs of FIG. 3, to which reference is now made, which illustrate the temperature variations on additions of single compounds and pairs of compounds to water. In single chemical systems, 30 g of the relevant compound was placed in 30 mL of water, whereas for two component systems 20 g of each of the two compounds were combined with 20 mL of water, so that the total mass is the same in each case. In each case the temperatures are recorded over the course of 60 minutes. In each case the temperature change $\Delta T$ is plotted against the time t. The temperature of the surroundings, and the initial temperature of the compounds and the water, is ambient temperature, i.e. approximately 20° C. It will be appreciated from the graphs that in some cases the temperature drops to below 0° C. for at least part of the time, as the temperature change $\Delta T$ is greater than −20 K.

The graphs show the effects of the single compounds ammonium chloride (AC), urea (U) and ammonium nitrate (AN); and show the effects for the combinations of ammonium chloride with urea (AC+U) and ammonium nitrate with urea (AN+U). It will be seen that the cooling effect of ammonium chloride is less than that of urea, and that both are less than that of ammonium nitrate, which is in conformity with the predictions shown in Table 1. However it is also apparent that combining urea with either ammonium chloride or ammonium nitrate increases the resultant temperature change. It is also apparent that the combination of urea with ammonium chloride (AC+U) produces a greater cooling effect than that of ammonium nitrate (AN) alone.

These measurements were obtained using urea from a commercially available product, and this urea was found to have an observed melting point in the range 116° C. to 125° C., which is significantly less than the textbook value for pure urea, which is 133-135° C. This suggests that the urea was not entirely pure. The urea was then subjected to a recrystallisation process using ethanol as a solvent, and this was found to raise the observed melting point to 128° C., clearly increasing the purity. The cooling effect of this purified urea was found to be significantly greater than that of that of the commercially sourced urea, giving a temperature minimum at $\Delta T=-18$ K as compared to $\Delta T=-14$ K as shown in FIG. 3. Consequently if a combination of this purified urea with ammonium chloride is used, the expected temperature variation is as shown by the graph P in FIG. 3.

A further consideration is the extent to which the chemical compounds are hygroscopic. Although the chemical compounds in the dry materials 30 are enclosed within the membranes 25 and 26, all practical membrane materials have some permeability to water vapour, so over a period of several months some water vapour may permeate the membranes 25 and 26 even if the permeability is low. It is therefore preferable to choose chemical compounds that are not significantly hygroscopic or subject to deliquescence. This can be assessed on the basis of the critical relative humidity (CRH) of the material, that is the humidity level at which the material begins to absorb moisture from the atmosphere. For some chemical compounds this may be relatively high in isolation, but can drop substantially in the presence of another chemical compound. For example the CRH figures for ammonium nitrate and urea are 54% and 78% respectively, when in isolation, but the CRH figure drops to 18% if these compounds are mixed together. Since normal ambient humidity is above 18% (but below 50%) these compounds are not hygroscopic in isolation, but are hygroscopic when mixed together. It has been found by experiment that the envisaged mixture of ammonium chloride and urea is not significantly hygroscopic, even in fairly high humidity environments.

Nevertheless it is clearly desirable to use a material for the membranes 25 and 26 that minimises the permeation of water vapour. Permeability is the volume of vapour that passes through the film per unit area per second, per unit pressure gradient. In this respect materials such as high-density polyethylene have moderately low permeability ($P=35\times10^{-10}$), whereas polyvinylidene chloride has a significantly lower permeability ($P=0.5\times10^{-10}$) in units of (cm$^3$·cm)/(cm$^2$·s·cm Hg). It may be advantageous to use a laminated film structure in order to attain a lower permeability for water vapour.

Thus the dry material 30 may desirably contain amounts of ammonium chloride and of urea that would independently provide a saturated solution. The precise proportions of these compounds may be adjusted according to the envisaged initial and final temperatures of the liquid, as this alters the solubility; the solubilities are higher with a warm liquid than a cold liquid, so to some extent the process is self-limiting as the temperature decreases, but as the liquid re-equilibrates with its surroundings and with the body temperature of the patient 10, more solid may be dissolved. By way of example 29.7 g of ammonium chloride may be combined with 108 g of urea, to which 100 mL of water would be subsequently added, for a situation in which the solution is expected to reach a final temperature of 20° C.; the actual quantities would depend on the volumes of the enclosures 18 and 20, but the same proportions may be maintained. The resulting saturated solution would contain 12.5% ammonium chloride, 45.4% urea and 42.1% water, by mass. The enclosures 18 and 20 would initially contain the ammonium chloride and urea in solid form, preferably each of the chemical components being of high purity, and be in the form of small particles, granules or powder. The enclosures 18 and 20 may be at least partially evacuated, initially, so there is little or no air in them.

The solubility of urea in water (see http://www.smart-fertilizer.com/articles/fertilizer-solubility) is reportedly about 78 g/100 mL at 0° C., about 85 g/100 ml at 10° C. and about 106 g/100 mL at 20° C., increasing further as the temperature rises; the solubility of ammonium chloride in water (see BASF technical information, M 1685 e (September 2002)) is 22.8 g/100 mL at 0° C., and similarly the solubility increases as the temperature rises being about 25.0 g/100 ml at 10° C. and 27.2 g/100 mL at 20° C. The optimum performance is obtained by approaching saturation for each compound at a desired temperature. Optimum performance has been obtained by providing an amount of urea that is within 10% of the amount required for saturation at 10° C., and providing an amount of ammonium chloride that is also within 10% of the amount required for saturation at 10° C.

Thus for example the garment 12 might initially contain 2.59 kg of urea, and 0.71 kg of ammonium chloride; and 3 L of water would be added to this. This corresponds to 86.3 g/100 mL of urea, which is 101.6% of the textbook figure for solubility at 10° C.; and 23.7 g/100 mL of ammonium chloride, which is 95% of the textbook figure for solubility at 10° C. It will be appreciated that these quantities are by way of example only, but that the quantities are preferably such as to achieve at least 90% of the solubility figure for each compound at 10° C.

A modified garment 12A differs from the garment 12 in that the enclosures 18 and 20 are subdivided. For example, referring now to FIG. 4 this shows a cross-sectional view corresponding to a view on the line 4-4 of FIG. 2, but showing the garment 12A after introduction of water. In this modification the outer flexible sheet 26 is bonded to the inner flexible sheet 25 along several parallel lines 33 so that each intervening portion 34 of the enclosure outer flexible sheet 26 forms a generally semicircular shape (in section) when water is introduced, so the enclosure 18 (or 20) is in the form of multiple parallel half-cylinders 35. The parallel lines 33, and consequently the longitudinal axes of the half-cylinders 35, may be straight or may be curved in plan view. This structure ensures that the enclosure 18 or 20, when full as a result of addition of water, has a well-defined volume. A separate sheet or strip 61 of compressed sponge corresponding to the sheet 60 is incorporated each of the subdivisions of the enclosures 18 and 20 that go to form the half-cylinders 35. As explained above, when the water is introduced into the enclosures 18 and 20, the compressed sponge expands to occupy substantially the bulk of the volume of the resulting half-cylinders 35, and the strips 61 in their expanded form are indicated by broken lines in two of these half-cylinders 35.

Figure 5:
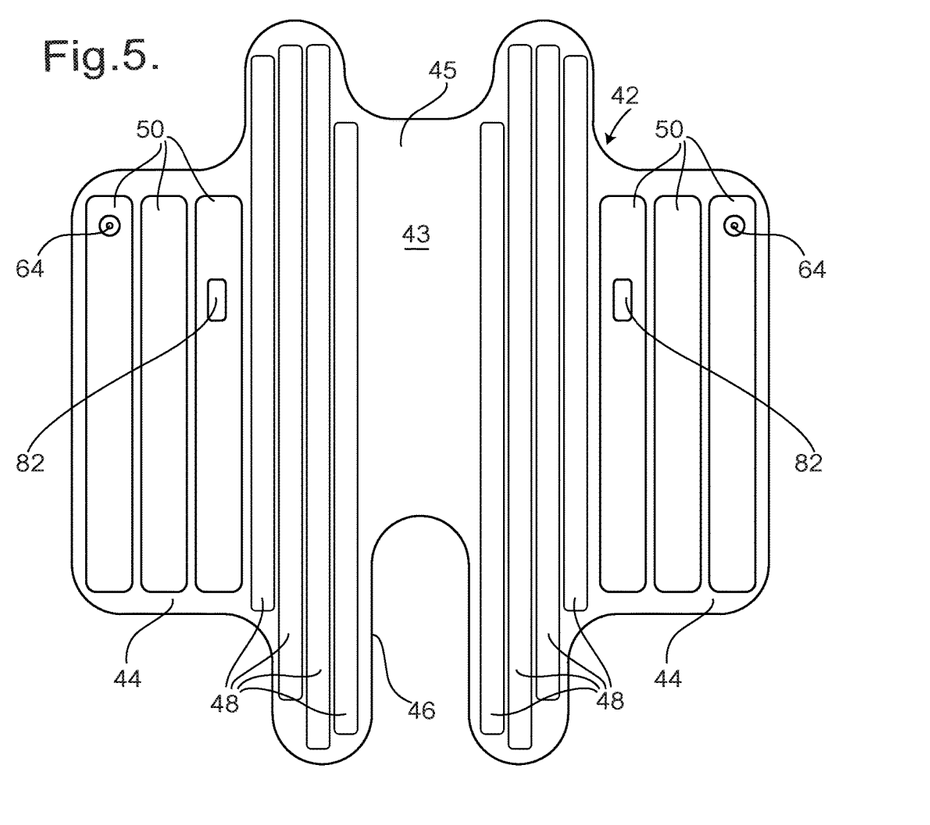
FIG. 5 shows a plan view of an alternative garment of the invention.

Referring now to FIG. 5 an alternative garment 42 includes a front portion 43 (as shown) which is intended to be placed on the torso of the patient 10 and side portions 44 which would extend around the sides of the patient's torso; the side portions 44 may be connected together across the back of the patient 10, for example by straps 14 and fasteners 15 equivalent to those shown in FIG. 1 (not shown in FIG. 5). The front portion 43 has a cut out 45 at the top for the patient's neck, and a cut out 46 extending from the bottom up to approximately the height of the patient's hips. The front portion 43 defines eight enclosures 48, between which is a region without any enclosures, where CPR can be applied to the patient. The enclosures 48 are sufficiently long that three of the enclosures 48 on each side extend (at the top) alongside the side of the patient's neck, and that three of the enclosures 48 on each side extend (at the bottom) over the patient's groin. The side portions 44 each define three enclosures 50 which in use lie alongside the patient's chest between armpit and hips. The garment 42 also includes a water inlet tube 21 with an inlet valve 22 (not shown in FIG. 5).

Figure 4:
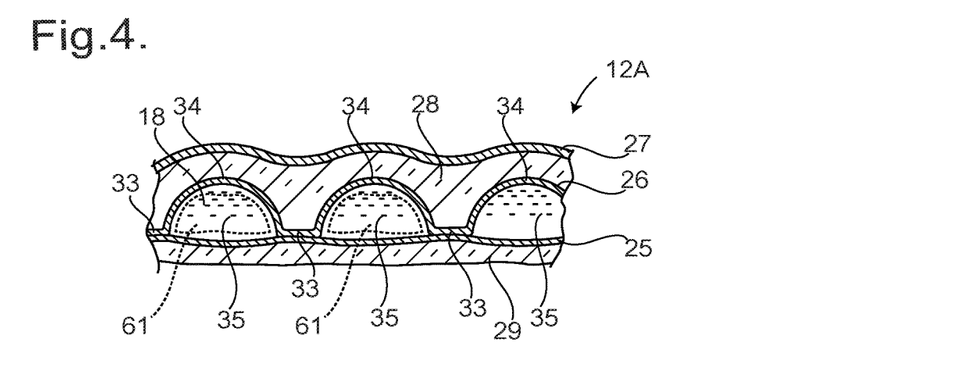
FIG. 4 shows a cross-sectional view through a modification to the garment of FIG. 1, corresponding to a view on the line 4-4 of FIG. 2.

The enclosures 48 and the enclosures 50 may have a structure equivalent to that shown in FIG. 4, as each enclosure 48 and 50 is a long straight rectangle with a rounded corners and all extending parallel to one another. Hence each enclosure 48 and 50 may be defined between inner and outer polymer films bonded together along the periphery of each enclosure 48 and 50. As explained above in relation to the jacket 12, each enclosure 48 and 50 contains dry material that includes urea and ammonium chloride, so that when water is introduced into the enclosure 48 or 50 an endothermic dissolution process takes place, withdrawing heat from the patient's torso. Each enclosure 48 and 50 also includes a strip of compressed sponge corresponding to the strips 61 referred to in relation to FIG. 4. The garment 42 may also include thermal insulation corresponding to the thermal insulation layers 28 and 29 described above.

It will be appreciated that a variety of different ways may be provided for introducing water into the enclosures 18, 20, 48, 50. In a first approach the enclosure is of a well-defined and predetermined volume, and water is introduced so as to fill that volume. In a second approach the volume of water that is introduced into each enclosure is predetermined, or monitored and controlled by an operator, to ensure the correct amount of water is introduced. And in a third approach the introduction of water is automated and controlled electronically.

As an example of the first approach, in the case of the garment 12A, the inlet valve 22 in the inlet tube 21 may be manually operable; and the inlet tube 21 may be connected to a container of water; the inlet valve 22 would then be opened, so water would flow through the channels 23 and 24 and fill the enclosures 18 and 20. The volume of the enclosures 18 and 20, when filled, is such that the amount of water introduced is that required for a saturated solution of the dry material 30. To express that differently, the amount of the dry material 30 is such that when the enclosures 18 and 20 are filled with water, the proportions of water and of the dry material 30 are such as to produce a saturated solution.

As an example of the second approach the garment 12 might be provided with separate inlet valves 22 for each enclosure, such as the enclosures 18 and 20, or with separate inlet tubes 21. The required quantity of water to achieve a saturated solution of the dry material 30 might for example be 400 mL in each enclosure. In this case the (or each) inlet tube 21 may be connected to a calibrated water container, and the inlet valves 22 opened by the operator so as to introduce the specified quantity of water into each enclosure, and the inlet valves 22 closed by the operator when the specified quantity of water has been introduced, the operator monitoring the quantity of water using the calibrations on the water container.

Alternatively an inlet tube 21 connected to an enclosure 18 or 20 may be connected to a water reservoir that contains the required quantity of water for that enclosure 18 or 20, and the inlet valve 22 opened so as to introduce the required quantity of water. This water reservoir may be in the form of a flexible pouch containing the required and predetermined quantity of water. Such a water reservoir may be an initial feature of the garment 12 or 42, or may be connected to the garment 12 or 42 when it is to be used.

As an example of the third approach the garment 12 may be provided with an electrically-powered pump, an electronic control module, electronically-controlled valves, and sensors to monitor the flow of water into each enclosure, such as the enclosures 18 and 20. These components may be powered for example by a disposable battery. After connecting the inlet tube 21 to a source of water, the control module would actuate the pump and open the electronically-controlled valves to pump the requisite quantity of water into each enclosure, and then close the electronically-controlled valves again.

The third approach may also be applicable in a context in which the enclosures, such as the enclosures 18 and 20 in the garment 12A, are of a well-defined and predetermined volume. In this case the control module would actuate the pump and open the electronically-controlled valves, and cease the introduction of liquid when a predetermined pressure is attained, indicating that the enclosures 18 and 20 are full.

The dry material 30 within each enclosure, such as the enclosures 18 and 20, may also include a gelling agent, so there is less risk of the saturated solution tending to flow to the bottom of the garment after water is added. For example a suitable gelling agent would be polyacrylic acid, but there are many other suitable options. Whichever gelling agent is utilised, this may be provided in an encapsulated form, encapsulated in a water-soluble membrane-forming material such as gelatin or hydroxypropyl-methyl-cellulose, to ensure that the gelling process is initiated only after the chemical compounds have dissolved, and thereby produced the requisite reduction in temperature. The provision of such a gelling agent may increase the heat capacity, and increase the duration of the cooling effect.

Each garment 12, 12A, 42 or 60 includes at least one inlet tube 21 with an inlet valve 22 through which water can be introduced into the enclosed compartments or enclosures 18 and 20, 48 and 50. This may be through flow ducts such as the channels 23 and 24 that are shown schematically in FIG. 1. Where there are multiple enclosures, such as the enclosures 48 and 50, the flow ducts may connect a plurality of enclosures in series, or in parallel, as regards the inflow of water. Each enclosure 18, 20, 48 and 50 may be provided with an air bleed valve 64 (as described below).

Referring again to FIG. 5, two such air bleed valves 64 are shown, each connected to one of the outermost enclosures 50; the provision of a single such air bleed valve 64 may be appropriate if the flow ducts (not shown) connect all the enclosures 48 and 50 on one side of the garment 42 in series, and the air bleed valve 64 is at the far end of the enclosure 50 furthest away from the inlet tube 21. The provision of the air bleed valves 64 constitutes a modification to the garment 42.

Figure 6:
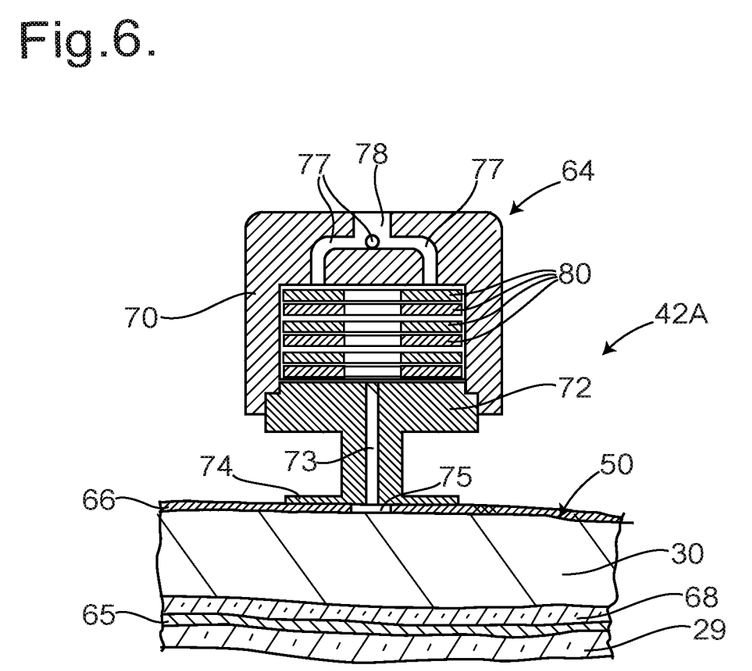
FIG. 6 shows a cross-sectional view through part of a modification to the garment of FIG. 5.

Referring now to FIG. 6, this shows a sectional view through a garment 42A which is a modification to the garment 42 of FIG. 5, identical features being referred to by the same reference numerals, the view only showing part of one enclosure 50, in which an air bleed valve 64 is provided. The enclosure 50 is shown prior to any addition of water, the enclosure 50 being defined between an inner flexible sheet 65 of a polymer and an outer flexible sheet 66 of a polymer. A layer 29 of thermal insulation such as felt is bonded to the inner flexible sheet 65, as in the garment 12. Within the enclosure 50 is a sheet 68 of compressed sponge, corresponding to the sheet 60 of FIG. 2 or the strip 61 of FIG. 4, and also the dry material 30 which consists of urea and ammonium chloride in powder form or granular form mixed together.

The air bleed valve 64 comprises a hollow cylindrical casing 70, open at one end, the open end of the casing 70 being closed and sealed by a bobbin 72 which defines a narrow axial hole 73. The bobbin 72 includes a stepped portion which is sealed into the open end of the casing 70, and a narrower projecting portion, at the end of which is a thin flange 74. The thin flange 74 is bonded to the outer flexible sheet 66, for example by heat welding, around a hole 75 through the outer flexible sheet 66. There are also narrow holes 77 (three are shown) that communicate through the end wall of the casing 70 with a recess 78 in the outside of that end wall. Consequently air can bleed out of the enclosure 50 through the narrow hole 73 to reach the cavity within the casing 70, and then out through the narrow holes 77 and the recess 78.

The cylindrical hollow casing 70 and the bobbin 72 may for example be of a plastic material, and may be bonded together for example by welding. The step of the stepped portion of the bobbin 72 ensures that the cavity within the casing 70 has a well-defined height. Within the cavity of the hollow casing 70 is a stack of annular washers 80 (six are shown) of a hygroscopic material that expands on contact with water. The dimensions of the cavity within the hollow casing 70 and the dimensions of the washers 80 are such that as long as the washers 80 remain dry, the bleed path for air is not obstructed. However, as soon as water reaches the washers 80, they expand and consequently block any airflow into the narrow holes 77. (The use of such washers of hygroscopic material has previously been described in the context of hot water radiator bleed valves, for example in U.S. Pat. Nos. 2,723,676 and 2,776,671.)

The garment 42A is not shown as including an outer layer of thermal insulation (corresponding to the layer 28 of FIG. 2), but it will be appreciated that such an outer layer of thermal insulation might be provided, and that the projecting portion of the bobbin 72 might extend through such a layer of thermal insulation. Where no such layer of thermal insulation is provided, the bobbin might not incorporate such a projecting portion, and the outer part of the stepped portion of the bobbin 72 might be connected directly to the outer flexible sheet 66.

As an alternative to the provision of the air bleed valve 64, the outer flexible sheet 26 or 66 that forms the enclosure 18, 20, 48, 50, in at least part of its area, may be formed of a gas-permeable hydrophobic polymer film. This may for example be a microporous hydrophobic membrane on a porous support sheet, for example a microporous PTFE membrane on a woven or nonwoven fabric backing. Another option would be to include a layer of polyurethane. Another option is the provision of hydrophobic porous rayon film.

Where a garment 12, 42 or 60 includes either an air bleed valve 64 or a region of gas-permeable hydrophobic film, to allow air to leave the enclosures, it will be appreciated that this may also allow water vapour to enter the enclosures, which could lead to problems of hygroscopicity. Although the combination of urea and ammonium chloride is not significantly hygroscopic, this problem can be avoided by providing a cover that is impermeable to water vapour over the air bleed valve 64 or the region of gas-permeable hydrophobic film, this cover being removed before use. In one example the cover may be of a plastic film such as a metallised plastic film. Alternatively this problem can be avoided by enclosing the entire garment 12 or 42 in packaging that is impermeable to water vapour, so that water vapour can only contact the garment once the packaging has been opened.

In a further modification a garment 12, 12A or 42 may include an indicator to indicate if the garment is too cold, or ready for use, or too warm. Such an indicator might be an electronic thermometer linked to a digital display (not shown), or a thermochromic device 82 as indicated schematically on each side of the garment 42.

In a modification at least some of the particles that form the dry mixture 30 are encapsulated in a water-soluble or water-permeable coating such as gelatin or hydroxypropyl-methyl-cellulose, to control the rate at which the dissolution process takes place, so it takes place more gradually. This ensures that the cooling effect is less abrupt, and is of longer duration. By way of example half of the particles may be encapsulated, so that they do not start to dissolve until say 10 minutes, 20 minutes or 30 minutes after the other half of the particles. More generally, some of the particles are not encapsulated, whereas some are encapsulated to delay dissolution by a certain time, and some are encapsulated to delay dissolution an even longer time.

The detailed description above is primarily concerned with a cooling device, but it will be appreciated that by selecting a dry material that comprises one or more compounds that dissolve exothermically, the result is a heating device. The benefits of the compressed sponge are the same in either case.

Other variations and modifications will be apparent to the skilled person. Such variations and modifications may involve equivalent and other features that are already known and which may be used instead of, or in addition to, features described herein. Features that are described in the context of separate embodiments may be provided in combination in a single embodiment. Conversely, features that are described in the context of a single embodiment may also be provided separately or in any suitable sub-combination.

It should be noted that the term "comprising" does not exclude other elements or steps, the term "a" or "an" does not exclude a plurality, a single feature may fulfil the functions of several features recited in the claims and reference signs in the claims shall not be construed as limiting the scope of the claims. It should also be noted that the Figures are not necessarily to scale; emphasis instead generally being placed upon illustrating the principles of the present invention.

The invention claimed is:

1. A thermal device comprising a garment that may be placed against at least a part of a body, the garment defining at least one enclosed compartment defined between an inner wall and an outer wall, the inner wall and the outer wall being flexible and being impermeable to liquid water, and an inlet tube including an inlet valve through which liquid water may be introduced into each such enclosed compartment, wherein each enclosed compartment contains dry material comprising at least one soluble chemical compound that dissolves endothermically or exothermically in the liquid water, the dry material being in powder or granular form and so being in the form of particles, and each enclosed compartment also contains at least one element of a compressed sponge, wherein the at least one element of compressed sponge, when dry, extends throughout the area of the enclosed compartment; the particles of the dry material within each compartment not being incorporated into the at least one element of compressed sponge; the arrangement being such that when liquid water a liquid is introduced into the enclosed compartment, it contacts both the dry material and also the at least one element of compressed sponge, and the at least one element of compressed sponge expands in thickness to occupy substantially the entire volume of the enclosed compartment.

2. A thermal device as claimed in claim 1 wherein each enclosed compartment communicates with an air bleed valve to enable any air within the enclosed compartment to be released, when a liquid such as water is introduced into that compartment.

3. A thermal device as claimed in claim 2 wherein the air bleed valve is arranged to operate automatically to allow air to bleed out, but to close when a liquid such as water enters the valve.

4. A thermal device as claimed in claim 3 wherein the air bleed valve includes one or more hygroscopic discs which allow air to flow when dry, but which expand to obstruct the flow when in contact with water.

5. A thermal device as claimed in claim 1 also including an indicator to indicate if the garment is too cold, or ready for use, or too warm.

6. A thermal device as claimed in claim 5 wherein the indicator is a thermochromic device.

7. A thermal device as claimed in claim 1 wherein the dry material comprises a covalently-bonded molecular compound and an ionic compound.

8. A thermal device as claimed in claim 7 which is a cooling device wherein the covalently-bonded molecular compound is urea and the ionic compound is ammonium chloride.

9. A thermal device as claimed in claim 1 wherein the garment defines a plurality of enclosed compartments.

10. A thermal device as claimed in claim 9 wherein the plurality of enclosed compartments are linked by sheet material.

11. A thermal device as claimed in claim 1, wherein the particles of the dry material are of substantially uniform particle size.

12. A thermal device as claimed in claim 1, wherein some of the particles of the dry material are encapsulated in a water-soluble or water-permeable coating, whereas some of the particles are not encapsulated.

13. A cooling device defining at least one enclosed compartment defined between an inner wall and an outer wall, the inner wall and the outer wall being flexible and being impermeable to liquid water, and an inlet tube including an inlet valve through which liquid water may be introduced into each such enclosed compartment, wherein each enclosed compartment contains dry material comprising soluble chemical compounds that dissolve endothermically in the liquid water, the dry material being in powder or granular form and so being in the form of particles, and each enclosed compartment also containing at least one element of a compressed sponge, wherein the at least one element of compressed sponge, when dry, extends throughout the area of the enclosed compartment; the particles of the dry material within each compartment not being incorporated into the at least one element of compressed sponge; the arrangement being such that when liquid water is introduced into the enclosed compartment, it contacts both the dry material and also the at least one element of compressed sponge, and the at least one element of compressed sponge expands in thickness to occupy substantially the entire volume of the enclosed compartment; wherein the soluble chemical compounds are urea and ammonium chloride, the mass of urea and of ammonium chloride within each compartment being selected in relation to the volume of liquid water to be added to that compartment such that the mass of urea is within 10% of the mass required for saturation at 10° C., and that the mass of ammonium chloride is within 10% of the mass required for saturation at 10° C.

14. A cooling device as claimed in claim 13, wherein the particles of the dry material are of substantially uniform particle size.

15. A cooling device as claimed in claim 13, wherein some of the particles of the dry material are encapsulated in a water-soluble or water-permeable coating, whereas some of the particles are not encapsulated.

* * * * *